United States Patent [19]

Tiéche

[11] 4,142,293
[45] Mar. 6, 1979

[54] ANCHORING SCREW FOR DENTAL FILLINGS

[76] Inventor: Jacques Tiéche, 74 560 Monnetier-Mornex, France

[21] Appl. No.: 773,131

[22] Filed: Feb. 28, 1977

[30] Foreign Application Priority Data

Mar. 3, 1976 [FR] France .............................. 76 07571

[51] Int. Cl.² .................................................. A61C 5/02
[52] U.S. Cl. ............................................. 32/15; 32/13
[58] Field of Search ................. 85/9 R, 45; 81/121, 81/71; 32/15, 11, 13, 6, 7

[56] References Cited

U.S. PATENT DOCUMENTS

| 906,040 | 12/1908 | Lucas | 81/121 R |
|---|---|---|---|
| 1,346,058 | 7/1920 | Robergol | 85/9 R |
| 2,103,944 | 12/1937 | Gullborg | 81/121 |
| 3,386,169 | 6/1968 | Scialon | 32/10 A |
| 3,532,012 | 10/1970 | Pryor | 81/121 R |

FOREIGN PATENT DOCUMENTS

| 665805 | 9/1938 | Fed. Rep. of Germany | 32/10 A |
|---|---|---|---|
| 745543 | 6/1946 | Fed. Rep. of Germany | 32/13 |
| 845243 | 3/1953 | Fed. Rep. of Germany | 32/13 |
| 1900712 | 1/1969 | Fed. Rep. of Germany | 32/15 |
| 1478557 | 8/1967 | France | 32/13 |
| 1431563 | 4/1976 | United Kingdom | 32/10 A |

Primary Examiner—Robert Peshock
Attorney, Agent, or Firm—Stevens, Davis, Miller & Mosher

[57] ABSTRACT

An anchoring screw for dental fillings has a head with two indented crowns separated by a narrow neck, and a tapered shank with a thread of saw-tooth profile. Actuation of the screw by a tubular spanner or socket can be achieved with the spanner or socket inclined by up to 40° to the screw axis.

3 Claims, 3 Drawing Figures

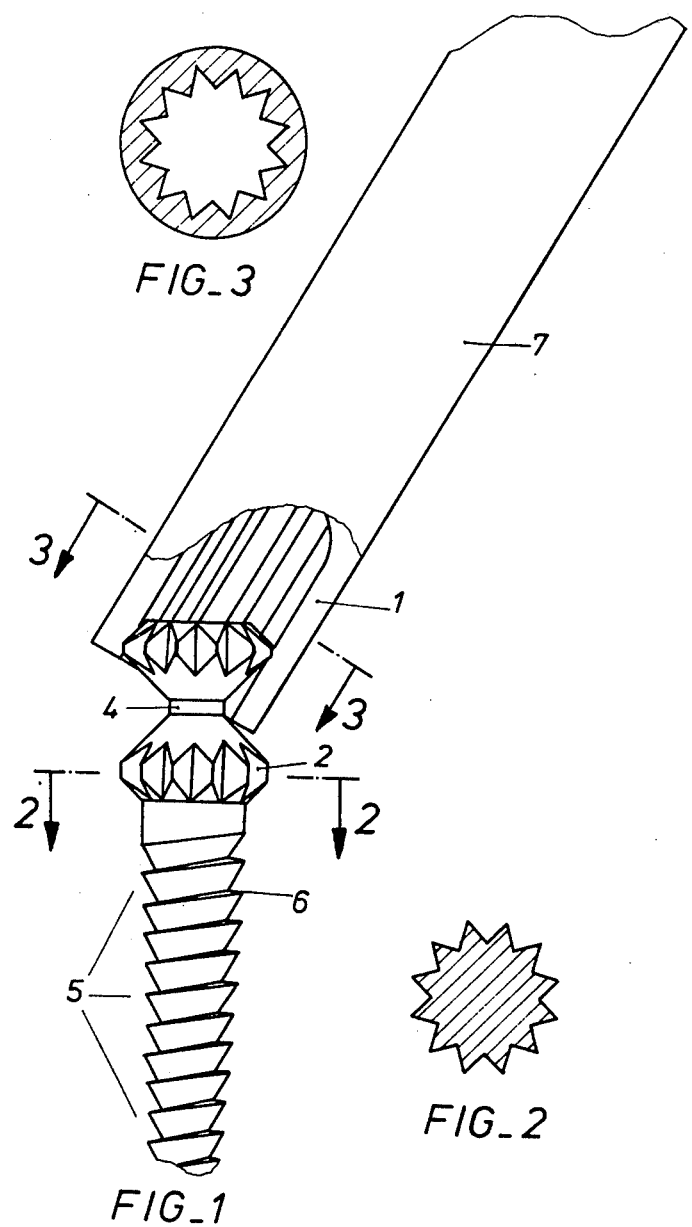
FIG_3
FIG_1
FIG_2

ANCHORING SCREW FOR DENTAL FILLINGS

The invention relates to anchoring screws for dental fillings.

Known anchoring screws for dental fillings are difficult to manoeuvre in a patient's mouth as the spanner serving to actuate them must make a fixed angle with the screw axis, to enable correct actuation.

An object of the invention is to remedy this drawback by providing an anchoring screw for dental fillings capable of being actuated by a spanner which can be inclined at will in relation to the screw axis within large limits, for example between zero and forty degrees.

According to the invention, an anchoring screw for dental fillings comprises a head formed of two crowns each having in transverse cross-section a non-circular profile for cooperation with an actuating spanner or locket, and a generally conical threaded shank extending from one of said crowns along an axis of the screw. The crowns are joined by a narrow neck defining a groove enabling cooperation of the other of said crowns with a generally tubular spanner while allowing the spanner to be inclined to the screw axis, and the threaded shank has a thread of sharp-angled generally saw-tooth profile.

The accompanying drawings show, by way of example, an embodiment of a dental-filling anchoring screw according to the invention. In the drawings:

FIG. 1 is a partly cut-away side view showing actuation of a screw by a spanner with the spanner inclined;

FIG. 2 is a cross-section along line 2—2 of FIG. 1; and

FIG. 3 is a cross-section of the spanner along line 3—3 of FIG. 1.

The illustrated anchoring screw for dental fillings comprises a head formed of two crowns 1, 2 having, in transverse cross-section, a star-like indented profile (FIG. 2). The crowns 1, 2 are separated by a narrow neck 4 defining a deep central groove. In side view, each crown 1, 2 has the general shape of two truncated cones whose large bases are placed together.

As shown in FIG. 1, this configuration enables the teeth of crown 1 to be operatively engaged by a corresponding inner toothing (FIG. 3) of a tubular spanner 7, while inclining this spanner 7 in relation to the screw at will between large limits, for example with the spanner axis at from 0 to 40 degrees to the screw axis. Hence, the operation of screwing the screw into a tooth is considerably facilitated.

The second profiled crown 2 and the groove adjacent neck 4 provide the following advantage. The neck 4 is a mechanically weak part of the screw. If an excessive force is inadvertently applied during screwing and the screw breaks, the rupture will most certainly occur in the neck 4. However, the broken screw can then easily be unscrewed by cooperation of the spanner 7 with crown 2. The shape of crown 2 enables the spanner 7 to be inclined at will during this operation.

A further advantage of the crown 2 is that if the position of the tooth in the mouth permits the spanner 7 to be used while it is disposed coaxial with the screw, the spanner 7 can be made to simultaneously cooperate with both crowns 1, 2.

The threaded shank 5 of the screw, which is screwed into a tooth in the manner that a wood screw penetrates a piece of wood, has a tapered generally conical shape and its thread has a "saw-tooth" profile with sharp angles 6, as shown. Hence, the screw is able to penetrate well into a tooth and cannot unscrew spontaneously.

Naturally, other shapes of crowns such as 1 and 2 can be envisaged, as long as these shapes enable actuation of the screw by a spanner while allowing the spanner to be inclined within large limits.

What is claimed is:

1. An anchoring screw for dental fillings, in combination with an actuating socket for screwing said screw into a tooth, said screw comprising a generally conical threaded shank having a thread of sharp-angled saw-tooth profile, a first crown formed on the upper end of the shank, a second crown formed coaxially above the first crown and separated from the latter by a narrow neck defining a circular groove between said first and second crowns, each crown having a circular toothed profile, said actuating socket being of substantially circular hollow cross-section with a toothed inside for actuating cooperation with said circular toothed profile of said second crown, said circular groove of said neck permitting said socket to be inclined at an angle of 0 to substantially about 40° from the screw axis in the operating position.

2. A screw according to claim 1 in which the two crowns have substantially the same shape.

3. A screw according to claim 1 in which each crown has the general shape of a double truncated cone.

* * * * *